United States Patent

Asami et al.

Patent Number: 5,178,854
Date of Patent: Jan. 12, 1993

[54] CHOLESTEROL-LOWERING AGENTS

[75] Inventors: Yumiko Asami, Saitama; Katsuo Komiya, Kanagawa; Hiroo Sasaki, Tokyo; Hironaka Aihara, Saitama, all of Japan

[73] Assignees: Taisho Pharmaceutical Co., Ltd.; Tosoh Corporation, both of Japan

[21] Appl. No.: 684,318

[22] Filed: Apr. 12, 1991

Related U.S. Application Data

[62] Division of Ser. No. 324,757, Mar. 17, 1989, abandoned.

[30] Foreign Application Priority Data

Mar. 24, 1988 [JP] Japan .................................. 63-70219

[51] Int. Cl.$^5$ .......................................... A61K 31/785
[52] U.S. Cl. ..................................................... 424/78.35
[58] Field of Search .................... 424/79, 78.35, 78.16

[56] References Cited

U.S. PATENT DOCUMENTS

| | | | |
|---|---|---|---|
| 3,780,171 | 6/1973 | Irmscher et al. | 424/79 |
| 4,055,429 | 10/1977 | Holmes et al. | 427/407 |
| 4,311,799 | 1/1982 | Miyake et al. | 521/38 |
| 4,412,011 | 10/1983 | Kihara | 521/38 |

OTHER PUBLICATIONS

Chemical Absracts, vol. 95, No. 9, 31 Aug. 1981, p. 125, No. 73880.
Chemical Abstracts, vol. 98, No. 16, 18 Apr. 1983, p. 373, No. 132320.

Primary Examiner—Thurman K. Page
Assistant Examiner—Peter F. Kulkosky
Attorney, Agent, or Firm—Lorusso & Loud

[57] ABSTRACT

A method for lowering serum total cholesterol in an animal by administering to the aminal an anion-exchange resin having the monomer units respectively represented by the below-given structural formulas (I), (II), (III) and (IV) in a content of 60-95 molar % of the monomer unit (I), 0-25 molar % of the monomer unit (II), 0—30 molar % of the monomer unit (III) and 1-6 molar % of themonomer unit (IV).

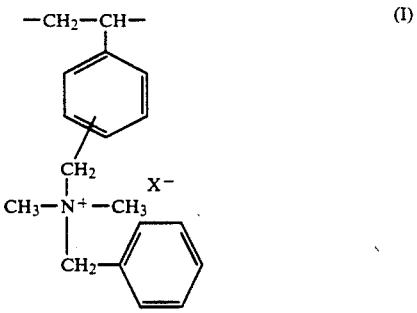

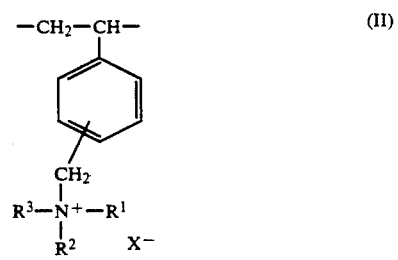

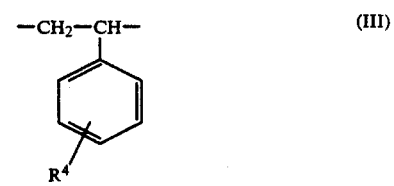

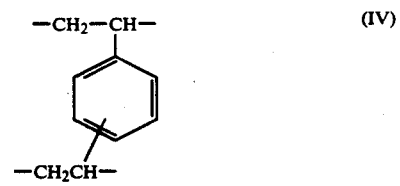

wherein $R^1$, $R^2$ and $R^3$ which may be the same or different respectively are hydrogen atom, a lower alkyl group or benzyl group, $R^4$ is hydrogen atom, a lower alkyl group or hydroxy-methyl group and X is a halogen atom. The above-mentioned agents specifically bind with bile acid in the intestinal tract even in the presence of other acids.

3 Claims, No Drawings

CHOLESTEROL-LOWERING AGENTS

This application is a division of application Ser. No. 07/324,757, filed Mar. 3, 1989, now abandoned.

BACKGROUND OF THE INVENTION

1. Field of the Invention

The present invention relates to cholesterol-lowering agents. More particularly, it is concerned with cholesterol-lowering agents containing an anion-exchange resin as an active component.

2. Description of Prior Art

Relationship between serum lipid and atherosclerotic diseases has been discussed for a long time. Recently, it has been elucidated scientifically that reduction of the serum cholesterol level can prevent the onset of coronary heart disease or the death from such disease [Journal of the American Medical Association (JAMA), vol. 251, pp. 351-364 (1984)].

It is also known that certain anion-exchange resins possess a serum cholesterol-lowering activity. Mechanism of the action is believed to lie in binding the anion-exchange resin with bile acids in the intestinal tract which in turn inhibits resorption of the bile acids and consequently promotes conversion of cholesterol existing in the liver in equilibrium with bile acids to bile acids thereby reducing serum cholesterol. Heretofore-known anion-exchange resins developed for removing bile acids in the intestinal tract by such binding are those disclosed in British Patent No. 929391, Japanese Patent Publication No. 54457/1986, Japanese Patent Laid-open to Public Nos. 150017/1981 and 142920/1982, etc. Typical of them is, for example, cholestiramine which is an amino resin (British Patent No. 929,391).

Whereas these resins have a large ion-exchanging capacity, they are not necessarily capable of selectively binding bile acids when acid substances are present in addition to bile acids in the intestinal tract. As a matter of fact, there are co-existing in the intestinal tract acid substances such as acidic proteins, amino acids and organic acids which bind with anion-exchange resin as a pair ion. Under such conditions, the amount of binding with bile acids is not necessarily large. It is therefore required that composition of the resin is designed so as to bind bile acids more selectively than binding other co-existing acid substances. Cholestiramine cannot necessarily be said to be satisfactory in percent inhibition of increase of serum total cholesterol.

It is an object of the invention to provide cholesterol-lowering agents more selectively binding bile acids thereby being more highly inhibitory against increase in serum total cholesterol.

DETAILED DESCRIPTION OF THE INVENTION

As a result of extensive studies in view of the above-mentioned object we have found that an anion-exchange resin with a specific composition possesses a remarkable serum cholesterol-lowering activity. The present invention has been completed on the basis of the finding.

Thus, the invention provides cholesterol-lowering agents comprising as an effective component anion-exchange resin composed of the monomer units respectively represented by the below-given structural formulas (I), (II), (III) and (IV) in a content of 60-95 molar % of the monomer unit (I), 0-25 molar % of the monomer unit (II), 0-30 molar % of the monomer unit (III) and 1-6 molar % of the monomer unit (IV).

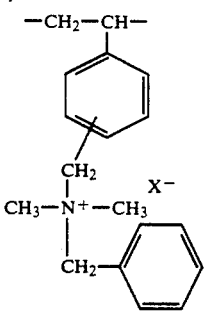

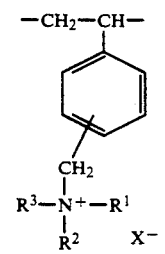

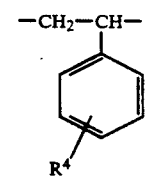

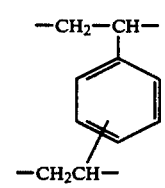

wherein $R^1$, $R^2$ and $R^3$ which may be the same or different respectively are hydrogen atom, a lower alkyl group or benzyl group, $R^4$ is hydrogen atom, a lower alkyl group or hydroxymethyl group and X is a halogen atom.

The lower alkyl as used in the invention is an alkyl group containing 1-4 carbon atoms such as methyl group, ethyl group and propyl groups. The halogen atom is chlorine atom, bromine atom, iodine atom or the like.

The anion-exchange resin according to the invention is preferably an entirely porous anion-exchange resin which contains as ion-exchange group 70 equivalent % or more of dimethylbenzylammonium group, has a total ion-exchange capacity of 1 milliequivalent/g on dry basis or higher, possesses a bridged polymer matrix composed as main monomer unit of styrene and divinylbenzene and is of an expulsion critical molecular weight in the range of 800 to 20000 in terms of polyethylene oxide in swelling in aqueous solution.

The anion-exchange resin according to the invention is disclosed in U.S. Pat. No. 4,055,429 as a development inhibitor scavenger in a photographic element and can be prepared by various methods. An example of the usually employed method is as follows: Styrene and divinylbenzene monomers in solution in the presence of an oil-soluble radical polymerization initiator is subjected to copolymerization in oil-in-water system, subsequently unreacted monomers and impurities are removed by washing, the residual mass is mixed with chloromethyl ether, and the mixture is subjected to chloromethylation using a Friedel-Crafts catalyst and then aminated by contact with dimethylbenzylamine. Alternatively, chloromethylstyrene and divinylbenzene monomers are copolymerized in the same manner as above, unreacted monomers and others are washed off and then the residual mass is contacted with dimethylbenzylamine. The monomers used in these methods may not necessarily be in high purity, especially so with divinylbenzene, purity of which is 55 wt % for general industrial use with approximately 45 wt % of ethylvinylbenzene contained and which is a favorable monomer provided that it is employed within a limit not exceeding 30 wt % of the entire monomers. In addition, vinyltoluene and the like may be used as a vinyl monomer of this nature.

Some of the chloromethylstyrene units may remain unreacted depending upon reaction conditions and nature of the tertiary amine in the reaction of a copolymer composed of monomer units such as chloromethylstyrene and divinylbenzene and a tertiary amine to form a quaternary ammonium group in the above preparative method. The units, however, produce no adverse influence upon cholesterol-lowering activity if the amount is not more than 15 molar % of the composing monomer units. Part of the chloromethyl group will also be hydrolyzed to form hydroxymethyl unit by-product if the amination reaction is conducted under basic conditions in the presence of water. The by-product, however, produces no adverse influence upon cholesterol-lowering activity provided that it is not more than 10 molar % of the entire composing monomer units.

Therefore, there may be contained in the anionexchange resin according to the invention the chloromethylstyrene monomer as an unreacted material in the amination and/or the hydroxymethylstyrene unit as a by-product.

There were produced various anion-exchange resins with different particle sizes by the method above mentioned. But, in using the anion-exchange resin as a cholesterol-lowering agent, appropriate particle size is 8–400 μm.

In using the anion-exchange resin as a cholesterol-lowering agent it is formulated in solid pharmaceutical preparations for oral administration dispersed in conventional carriers and diluents such as tablets, powders, granules and capsules. The anion-exchange resin may also be added to drinkable liquors such as fruit juice and other drinks. They are prepared by a conventional pharmaceutical technique.

As the carriers used in preparing the solid pharmaceutical preparations for oral administration are mentioned excipients such as lactose, glucose, crystalline cellulose, mannitol, corn starch and sugar, binding agents such as hydroxypropylcellulose, hydroxypropylmethylcellulose, carboxymethylcellulose, polyvinyl alcohol, gelatin and gum arabic, wetting agents such as glycerin and ethylene glycol, disintegrating agents such as corn starch, potato starch, calcium carboxymethylcellulose and low-degree substituted hydroxypropylcellulose, and lubricants such as calcium stearate, magnesium stearate, talc, polyethylene glycol and hardened oil. In addition, additives such as surfactants, coloring agents and taste-improving agents may be employed, as required.

In order to treat hypercholesteremia the anionexchange resin according to the invention is orally administered in adults at a daily dose of 0.6–15 g in one to several divided doses. The dosage may appropriately be increased or decreased depending upon age, body weight and conditions of patients. The anion-exchange resin according to the invention has a very low toxicity to mammals including man which is generally at a level lower than 10 g/kg body weight in rats for acute toxicity ($LD_{50}$) by oral route.

The invention will be described below in more details with reference to preparative examples and examples, which, however, are not limiting ones.

Preparative Example 1

A mixture of 50 parts by weight of styrene, 3.5 parts by weight of divinylbenzene of 55% purity and 0.5 parts by weight of benzoyl peroxide was prepared in solution and was poured into 150 parts by weight of a 2% by weight aqueous solution of polyvinyl alcohol. The resulting mixture was reacted with vigorous stirring for 20 hours while heating to 80° C. There were produced globular particles of a bridged polymer with particle sizes of 150 micron or smaller. The particles were thoroughly washed on a glass filter with pure water and acetone to remove the polyvinyl alcohol, unreacted monomers and impurities and dried under reduced pressure. To 5 parts by weight of the particles were added 30 parts by weight of chloromethyl ether and 5 parts by weight of zinc chloride. The mixture was reacted at 50° C. for 8 hours, and then washed with acetone. There were obtained chloromethylated styrene polymer particles with a chlorine content of 20%.

With 5 parts by weight of the particles were mixed 50 parts by weight of pure water and 4 parts by weight of N,N-dimethylbenzylamine. The mixture was reacted at 40° C. for 24 hours, and then washed with 0.1N hydrochloric acid and pure water to remove excess amine. There was thus obtained an anion-exchange resin of the invention.

The anion-exchange resin thus obtained contained 80.7 molar % of a monomer unit of the formula (I), 0 molar % of a monomer unit of the formula (II), 2.3 molar % of a monomer unit of the formula (III), 2.8 molar % of a monomer unit of the formula (IV), and additionally 9.6 molar % of unreacted chloromethylstyrene unit and 4.6 molar % of hydroxymethylstyrene unit.

Physical properties of the resin are as follow:
Total ion exchange capacity:
1.2 milliequivalent/g (on dry basis)
Expulsion critical molecular weight:
7000 (molecular weight of polyethylene oxide in aqueous solution)
Pore volume: 3.2 ml/g (in aqueous solution)
Apparent density: 0.22 g/ml
Particle size distribution: 30–130μm

[Measurement of the expulsion critical molecular weight was made by the gel permeation chromatographic method described in "High Performance Liquid Chromatography" (edited by J. J. Kirkland, Kodansha, pp. 203–204). As the standard sample of polyethylene oxide was used one manufactured by Wako Pure Chemical Industries, Ltd. or TOSOH, as the eluent was used 0.1M aqueous solution-of sodium chloride and measurement was made at room temperature. The same procedures were employed in the below, too.]

Preparative Example 2

A mixture of 148 parts by weight of chloromethylstyrene, 5.5 parts by weight of divinylbenzene of 55% purity and 5.0 parts by weight of 2,2'-azobisisobutylnitrile was prepared in solution and was poured into 370 parts by weight of 5% by weight aqueous solution of polyvinyl alcohol. The resulting mixture was reacted with vigorous stirring for 10 hours while heating to 80° C. There were obtained globular particles of a bridged polymer with particle sizes of 60 micron or smaller. The particles were thoroughly washed on a glass filter with pure water and acetone to remove the polyvinyl alcohol. Then, a mixture of 190 parts by weight of the bridged polymer globular particles obtained (suction dry cake on the glass filter), 2400 parts by weight of pure water and 110 parts by weight of N,N-dimethylbenzylamine was reacted at 25° C. for 16 hours followed by addition of 25 parts by weight of triethylamine hydrochloride and 10 parts by weight of solid sodium hydroxide. The mixture was reacted at 25° C. for 4 hours, and the reaction product was then washed successively with 0.1N hydrochloric acid, acetone and pure water and dried. There was obtained an anion-exchange resin of the invention.

The anion-exchange resin obtained contained 78.8 molar % of a monomer unit of the formula (I), 11.9 molar % of a monomer unit of the formula (II), 2.0 molar % of a monomer unit of the formula (III), 2.4 molar % of a monomer unit of the formula (IV), and additionally 1.6 molar % of unreacted chloromethylstyrene unit and 3.6 molar % of hydroxymethylstyrene unit.

Physical properties of the resin were as follows:
Total ion exchange capacity: 1.9 milliequivalent/g (on dry basis)
Expulsion critical molecular weight: 7000 (molecular weight of polyethylene oxide in aqueous solution)
Pore volume: 5.2 ml/g (in aqueous solution)
Apparent density: 0.14 g/ml
Particle size distribution: 25-140 μm Preparative Example 3

A mixture of 370 parts by weight of chloromethylstyrene, 16 parts by weight of divinylbenzene of 55% purity and 13 parts by weight of 2,2'-azobis-2,4-dimethylvaleronitrile was prepared in solution and poured into 1100 parts by weight of 4% by weight aqueous solution of polyvinyl alcohol. The resulting mixture was reacted with vigorous stirring for 16 hours while heating to 55° C. There were obtained globular particles of a bridged polymer with particle sizes of 70 micron or smaller. The particles were thoroughly washed on a glass filter with pure water to remove the polyvinyl alcohol. Then, 250 parts by weight of the bridged polymer globular particles obtained (suction dry cake on the glass filter), 3200 parts by weight of pure water and 146 parts by weight of N,N-dimethylbenzylamine were mixed, and the mixture was reacted at 25° C. for 16 hours followed by addition of 70 parts by weight of 30% aqueous solution of trimethylamine. The mixture was reacted at 25° C. for 4 hours, and the reaction product was washed successively with 0.1N hydrochloric acid, acetone and pure water and dried. There was obtained an anion-exchange resin of the invention.

The anion-exchange resin thus obtained contained 85.0 molar % of a monomer unit of the formula (I), 7.9 molar of a monomer unit of the formula (II), 2.3 molar % of a monomer unit of the formula (III), 2.8 molar % of a monomer of the formula (IV) and additionally 0.4 molar % of unreacted chloromethylstyrene unit and 2.8 molar % of hydroxymethylstyrene unit.

Physical properties of the resin were as follow:
Total ion exchange capacity: 2.5 milliequivalent/g (on dry basis)
Expulsion critical molecular weight: 3600 (molecular weight of polyethylene oxide in aqueous solution)
Pore volume: 3.7 ml/g (in aqueous solution)
Apparent density: 0.18.g/ml
Particle size distribution: 25-140 μm

EXAMPLE 1

Six hundred grams of the resin produced in Preparative Example 1, 120 g of crystalline cellulose and 126 g of corn starch were blended to a uniform powdery blend. The blend was granulated with 45 g of hydroxypropylcellulose as a binding agent by the wet granulation method. The granules, after blended with 9 g of magnesium stearate, were tableted to tablets each 9 mm in diameter and 300 mg by weight.

EXAMPLE 2

One thousand grams of the resin produced in Preparative Example 1, 50 g of crystalline cellulose, 45 g of corn starch and 5 g of magnesium stearate were uniformly blended. The powdery blend was filled in hard capsules of an appropriate size in an amount of 550 mg per capsule.

EXAMPLE 3

One thousand and two hundred grams of the resin produced in Preparative Example 2, 300 g of mannitol and 450 g of corn starch were blended to a uniform powdery blend. The blend was granulated with 50 g of hydroxypropylcellulose as a binding agent by the wet granulation method.

EXAMPLE 4

Two thousand and two-hundred grams of the resin produced in Preparative Example 1 and 800 g of lactose were uniformly blended to give a powdery preparation. The preparation was divided into packs each weighing 3000 mg.

EXAMPLE 5

| | |
|---|---|
| The resin produced in Preparative Example 3 | 2000 g |
| Lactose | 960 g |
| Powdery gum arabic | 25 g |
| Parahydroxybenzoic acid | 10 g |
| Flavoring | 5 g |

The above materials were uniformly blended and divided into packs each weighing 3000 mg to give a dry syrup preparation.

The anion-exchange resin according to the invention is effective in treating hypercholesteremia in mammalian animals including a man caused by various factors and can be used as an agent for treating the disease. Furthermore, it exerts much better inhibition of the increase in serum total cholesterol as compared with known agents for treating hypercholesteremia. More-over, it specifically inhibits low-density blood lipoprotein which causes atherosclerosis.

The anion-exchange resin according to the invention exerted a marked cholesterol-lowering action by oral administration in the disease model experimentally produced by cholesterol loading.

The test examples will be shown below.

TEST EXAMPLE 1

[Action in Cholesterol-Fed Hypercholesteremic Rats]

Groups of 6 Wistar male rats (3 weeks old, weighing approximately 75 g) were used as test animals. The animals were placed in the test during which water and the below-listed feeds (1)-(6), respectively were given ad lib.

(1) Rat Powdery feed (manufactured by Oriental Yeast Co., Ltd.) (Normal feed group)
(2) Feed prepared by adding to the rat powdery feed 1% cholesterol and 0.5% sodium cholate (High-cholesterol group)
(3) Feed prepared by adding to the high-cholesterol feed (2) 2% of the anion-exchange resin produced in Preparative Example 1 (Present invention group 1)
(4) Feed prepared by adding to the high-cholesterol feed (2) 2% of the anion-exchange resin produced in Preparative Example 2 (Present invention group 2)
(5) Feed prepared by adding to the high-cholesterol feed (2) 2% of the anion-exchange resin produced in Preparative Example 3 (Present invention group 3)
(6) Feed prepared by adding to the high-cholesterol feed (2) 2% of cholestiramine (Control group)

The animals were ad lib. fed with the feed for 5 days. Then, blood was drawn under ether anesthesia, and serum was separated. Serum cholesterol, was measured by the enzymatic method using an autoanalyzer (Hitachi Model 7150), and percent inhibition of the increase was calculated according to the equation given below.

Inhibition of the increase (%) =

$$\frac{\text{(High-cholesterol group)} - \text{(Present invention group or control group)}}{\text{(High-cholesterol group)} - \text{(Normal feed group)}} \times 100$$

Results are shown in Table 1.

TABLE 1

Action in hypercholesteremic rats

| Group | Number of animals | Serum total cholesterol (mg/dl) | Inhibition of increase |
|---|---|---|---|
| Normal feed group | 6 | 94.2 ± 2.5* | — |
| High-cholesterol group | 6 | 492.0 ± 15.9 | — |
| Present invention group 1 | 6 | 109.0 ± 7.7* | 96.3 |
| Present invention group 2 | 6 | 123.0 ± 11.2* | 92.7 |
| Present invention group 3 | 6 | 157.9 ± 9.3* | 84.0 |
| Control group | 6 | 230.7 ± 23.0 | 65.7 |

*$P < 0.001$ (Significantly different over high-cholesterol group)

TEST EXAMPLE 2

[Action in Cholesterol-Fed Hypercholesteremic Rabbits]

Thirty NZW male rabbits (weighing approximately 3 kg) divided into 6 groups of 5 animals were placed in the test. Each group was respectively given the feeds (7)-(12) as listed below in an amount of 100 g/day for 2 weeks. Blood was drawn from the auricle vein early in the morning in hunger prior to and every week after initiation of the test. Sorum was separated, and serum cholesterol level was measured by the enzyme method using an autoanalyzer (Hitachi Model 7150). Percent inhibition of the increase was calculated according to the equation given in Test Example 1.

(7) Rabbit solid feed (manufactured by Oriental Yeast Co., Ltd.) (Normal feed group)
(8) Feed prepared by adding to the rabbit solid feed 1% of cholesterol (High-cholesterol group)
(9) Feed prepared by adding to the high-cholesterol feed (8) 0.25% of the anion-exchange resin produced in Preparative Example 1 (Present invention group 4)
(10) Feed prepared by adding to the high-cholesterol feed (8) 0.5% of the anion-exchange resin produced in Preparative Example 1 (Present invention group 5)
(11) Feed prepared by adding to the high-cholesterol feed (8) 0.5% of the anion-exchange resin produced in Preparative Example 2 (Present invention group 6)
(12) Feed prepared by adding to the high-cholesterol feed (8) 1% of cholestiramine (Control group)

From the serum obtained on the last day was separated blood high-density lipoproteins (HDL) by the precipitation method. Cholesterol level in the lipoproteins was measured in the same way as above, and at the same time cholesterol level in very low density lipoproteins plus low-density lipoproteins (VLDL +LDL) was calculated.

Results are shown in Table 2 and Table 3.

TABLE 2

Action in hypercholesteremic rabbits

| Group | Serum total cholesterol (mg/dl) | | |
|---|---|---|---|
| | Week 0 | Week 1 | Week 2 |
| Normal feed group | 30.3 ± 2.1 | 31.0 ± 6.9* | 35.8 ± 4.5** |
| High-cholesterol group | 37.5 ± 4.4 | 632.3 ± 105.6 | 1020.3 ± 100.3 |
| Present invention group 4 | 29.0 ± 5.5 | 407.2 ± 168.6 (37.4) | 705.0 ± 75.6* (32.0) |
| Present invention group 5 | 34.0 ± 4.7 | 333.5 ± 62.1* (49.7) | 495.0 ± 83.9** (53.4) |
| Present invention group 6 | 42.2 ± 7.6 | 478.3 ± 69.8 (25.6) | 725.9 ± 70.3* (29.9) |
| Control group | 31.3 ± 4.2 | 571.0 ± 98.3 (10.2) | 986.3 ± 114.5 (3.5) |

In the parentheses is given percent inhibition of the increase.
*$P < 0.05$ (Significantly different over high-cholesterol group)
**$P < 0.01$ (Significantly different over high-cholesterol group)

TABLE 3

Action on lipoprotein in hypercholesteremic rabbits

| Group | HDL-cholesterol (mg/dl) | VLDL + LDL-cholesterol (mg/dl) |
|---|---|---|
| Normal feed group | 21.5 ± 0.6* | 14.3 ± 4.8** |
| High-cholesterol group | 40.5 ± 3.5 | 979.8 ± 102.3 |
| Present invention group 4 | 42.9 ± 6.9 | 652.5 ± 95.6*(33.9) |
| Present invention group 5 | 35.0 ± 4.6 | 460.0 ± 79.9**(53.8) |
| Present invention group 6 | 36.4 ± 5.7 | 689.5 ± 63.5*(30.1) |

TABLE 3-continued

Action on lipoprotein in hypercholesteremic rabbits

| Group | HDL-cholesterol (mg/dl) | VLDL + LDL-cholesterol (mg/dl) |
|---|---|---|
| Control group | 32.3 ± 4.6 | 954.0 ± 112.2(2.7) |

In the parentheses is given percent inhibition of the increase.

*$P<0.05$ (Significantly different over high-cholesterol group)

**$P<0.01$ (Significantly different over high-cholesterol group)

TEST EXAMPLE 3

Acute Toxicity

Groups of 10 Wistar male rats (weighing 160-180 g) were placed in the test. Test drugs were prepared in various concentrations by suspending the anion-exchange resin produced in Preparative Example 1 in 5% aqueous solution of gum arabic. Each group of the animals was given the drug once orally at doses increasing in a geometric ratio. The animals were observed for 14 days, and the $LD_{50}$ was determined.

As a results of the above experiment, the $LD_{50}$ was not lower tan 10 g/kg.

We claim:

1. A method for lowering serum total cholesterol in an animal comprising administering to said animal, in an amount effective for said lowering, a cholesterol-lowering agent comprising an anion-exchange resin composed of the monomer units respectively represented by the below-given structural formulas (I), (II), (III) and (IV) in a content of 60-95 molar % of the monomer unit (I), 0-25 molar % of the monomer unit (II), 0-30 molar % of the monomer unit (III) and 1-6 molar % of the monomer unit (IV)

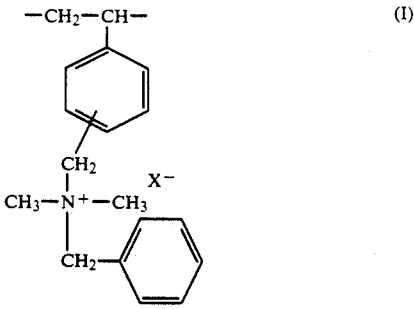

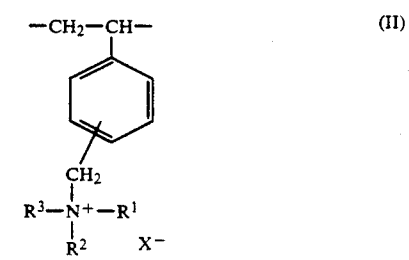

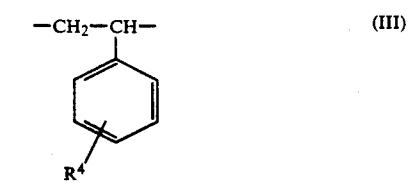

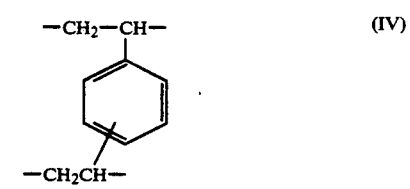

wherein $R^1$, $R^2$ and $R^3$ which may be the same or different respectively are hydrogen atom, a lower alkyl group or benzyl group, $R^4$ is hydrogen atom, a lower alkyl group or hydroxy-methyl group and X is a halogen atom.

2. The method of claim 1 wherein the anion-exchange resin contains 70 equivalent % or more dimethylbenzylammonium groups, has a total ion-exchange capacity of at least 1 milliequivalent/g, dry basis, possesses a polymeric matrix formed mainly of styrene and divinylbenzene monomers and has an expulsion critical molecular weight in the range of 800 to 20,000 in terms of polyethylene oxide.

3. The method of claim 1 wherein said agent contains 1-25 molar % of the monomer unit (II) and 1-30 molar % of the monomeric unit (III).